United States Patent
Sokulin et al.

(10) Patent No.: US 9,949,718 B2
(45) Date of Patent: Apr. 24, 2018

(54) METHOD AND SYSTEM FOR CONTROLLING COMMUNICATION OF DATA VIA DIGITAL DEMODULATION IN A DIAGNOSTIC ULTRASOUND SYSTEM

(75) Inventors: Alexander Sokulin, Kiryat Tivon (IL); Kjell Kristoffersen, Oslo (NO); Arcady Kempinski, Haifa (IL); Shabtay Eliad, Zichron Yaakov (IL)

(73) Assignee: General Electric Company, Schenectady, NY (US)

( * ) Notice: Subject to any disclaimer, the term of this patent is extended or adjusted under 35 U.S.C. 154(b) by 2255 days.

(21) Appl. No.: 12/834,623

(22) Filed: Jul. 12, 2010

(65) Prior Publication Data

US 2012/0010508 A1    Jan. 12, 2012

(51) Int. Cl.
*A61B 8/14* (2006.01)
*A61B 8/00* (2006.01)
*A61B 8/08* (2006.01)

(52) U.S. Cl.
CPC ............ *A61B 8/4405* (2013.01); *A61B 8/461* (2013.01); *A61B 8/467* (2013.01); *A61B 8/469* (2013.01); *A61B 8/486* (2013.01); *A61B 8/52* (2013.01); *A61B 8/56* (2013.01)

(58) Field of Classification Search
None
See application file for complete search history.

(56) References Cited

U.S. PATENT DOCUMENTS

| | | | |
|---|---|---|---|
| 5,437,281 A * | 8/1995 | Lin et al. | 600/443 |
| 5,549,111 A * | 8/1996 | Wright et al. | 600/443 |
| 5,797,847 A | 8/1998 | Miller et al. | |
| 5,928,152 A | 7/1999 | Wright et al. | |
| 6,142,946 A | 11/2000 | Hwang | |
| 7,009,533 B1 | 3/2006 | Wegener | |
| 7,394,410 B1 | 7/2008 | Wegener | |
| 7,477,999 B2 | 1/2009 | Wegener | |
| 2008/0110263 A1 | 5/2008 | Klessel et al. | |
| 2008/0114250 A1 | 5/2008 | Urbano et al. | |
| 2008/0114253 A1 | 5/2008 | Randall et al. | |
| 2008/0114255 A1 * | 5/2008 | Schwartz et al. | 600/474 |
| 2010/0121194 A1 | 5/2010 | Kondo | |
| 2013/0030257 A1 * | 1/2013 | Nakata et al. | 600/301 |
| 2013/0226001 A1 * | 8/2013 | Steen et al. | 600/447 |

FOREIGN PATENT DOCUMENTS

| | | |
|---|---|---|
| CN | 1279844 A | 1/2001 |
| CN | 1316227 A | 10/2001 |
| CN | 1889887 A | 1/2007 |
| JP | 11299776 | 11/1999 |

* cited by examiner

*Primary Examiner* — Serkan Akar
(74) *Attorney, Agent, or Firm* — Joseph M. Butscher; The Small Patent Law Group, LLC

(57) ABSTRACT

Methods and systems for controlling communication of data in an ultrasound system are provided. One method includes receiving ultrasound data from a plurality of channels of an ultrasound probe in an ultrasound system and digitally demodulating the received ultrasound data such that a data transfer rate of the digitally demodulated ultrasound data is lower than a data transfer rate of the received ultrasound data before digital demodulation. The method further includes processing the digitally demodulated ultrasound data, wherein the processing is performed using a processor of the ultrasound system.

8 Claims, 9 Drawing Sheets

METHOD AND SYSTEM FOR CONTROLLING COMMUNICATION OF DATA VIA DIGITAL DEMODULATION IN A DIAGNOSTIC ULTRASOUND SYSTEM

BACKGROUND OF THE INVENTION

The subject matter disclosed herein relates generally to ultrasound systems, and more particularly to methods and systems for communicating data within an ultrasound system, particularly transferring data from a front end of the ultrasound system to a back end for processing.

Diagnostic medical imaging systems typically include a scan portion and a control portion having a display. For example, ultrasound imaging systems usually include ultrasound scanning devices, such as ultrasound probes having transducers that are connected to an ultrasound system to control the acquisition of ultrasound data by performing various ultrasound scans (e.g., imaging a volume or body). The ultrasound systems are controllable to operate in different modes of operation and to perform different scans. The signals received at the front end of the ultrasound system are then communicated to and processed at a back end.

In conventional ultrasound systems, the front end generally includes an application specific integrated circuit (ASIC) or a field-programmable gate array (FPGA) that beamforms the received signals. However, this hardware implemented beamformer provide less flexibility. For example, the type of beamforming that is implemented is limited to the particular hardware implementation, such that only a specific beamforming is capable of being performed. Thus, the hardware components in the front end are specialized and do not allow changes to the beamforming algorithm once the algorithm is installed within the ASIC or FPGA.

Moreover, multiple beams may be created at the same time, for example, during four-dimensional (4D) imaging. In hardware implemented beamformers, the creation of these multiple beams at the same time requires intensive or significant processing, which can result in a costly implementation and an increase in the size of the ultrasound system.

In software implemented beamformers, the beamformer is implemented in the back end of the ultrasound system. In these software implemented beamformers, all of the channels of beamformed data created from the received signals must be communicated from the front end to the back end for backend processing. The amount of data that needs to be communicated from the front end to the back end in these software implemented beamformers is large and can increase significantly depending on the type of scanning being performed. Accordingly, higher bandwidth buses, more communication lines and/or higher processing power are required to operate these ultrasound systems. These components can also add size and cost to the ultrasound system. Moreover, the data rates needed to transfer the amount of data to be processed may exceed the highest data transfer rate of the communication lines (e.g., a Peripheral Component Interconnect (PCI) bus) of the system.

BRIEF DESCRIPTION OF THE INVENTION

In accordance with various embodiments, a method for processing ultrasound data is provided. The method includes receiving ultrasound data from a plurality of channels of an ultrasound probe in an ultrasound system and digitally demodulating the received ultrasound data such that a data transfer rate of the digitally demodulated ultrasound data is lower than a data transfer rate of the received ultrasound data before digital demodulation. The method further includes processing the digitally demodulated ultrasound data, wherein the processing is performed using a processor of the ultrasound system.

In accordance with other various embodiments, a method for demodulating ultrasound data is provided. The method includes receiving ultrasound data from a plurality of channels of an ultrasound probe in an ultrasound system and reducing a sample rate of the received ultrasound data for the plurality of channels using digital demodulation. The method also includes communicating the reduced sample rate ultrasound data to a processor of the ultrasound system and performing processing of the reduced sample rate ultrasound data using the processor, wherein the processing includes beamforming.

In accordance with yet other various embodiments, an ultrasound system is provided that includes an ultrasound probe for acquiring ultrasound data for an object of interest and an analog to digital converter (ADC) configured to receive a plurality of channels of analog ultrasound data from the ultrasound probe and convert the analog ultrasound data into digital ultrasound data. The ultrasound system further includes a demodulator configured to reduce a sample rate of the digital ultrasound data lower than a sample rate of the ADC and a processor configured to beamform the reduced sample rate digital ultrasound data.

DETAILED DESCRIPTION OF THE INVENTION

Figure 1:
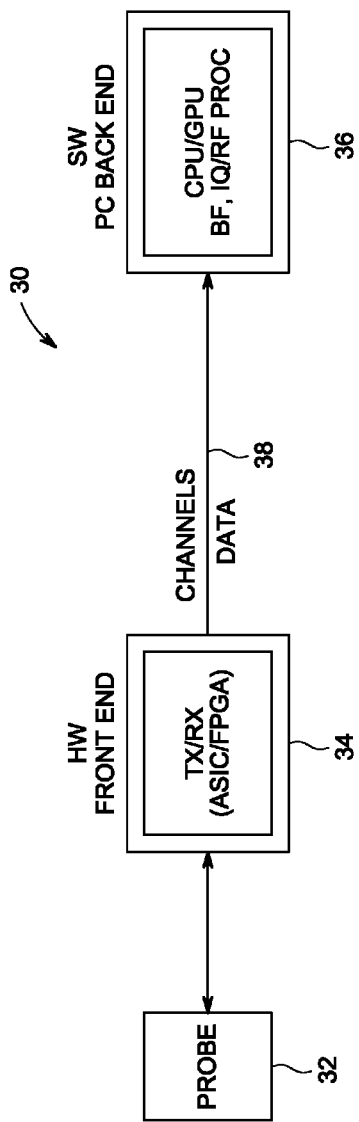
FIG. 1 is a simplified block diagram of an ultrasound system formed in accordance with various embodiments.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Various embodiments provide a system and method for communicating data within an ultrasound system for processing. Some embodiments control the amount of data transmitted for processing by a software beamformer. For example, in some embodiments, a reduced amount of ultrasound data is communicated to a software beamformer for processing, with the software beamformer implemented in a general processing or general purpose central processing unit (CPU) or a graphics processing unit (GPU). Such processing to form images may include, for example, for each desired image reconstruction point, generating a general linear combination of time delayed and/or phase shifted channel data, where the channel data may originate from the same or different ultrasound transmit events, and where the time delay/phase shifting is selected to focus the image at or close to the image reconstruction point. The set of image reconstruction points also may include scan lines (vectors), pixels of the display or other suitable geometries.

A technical effect of at least some embodiments is reducing the amount of received data communicated from a front end of an ultrasound system for processing at a back end of the ultrasound system by processing units. A technical effect of at least some embodiments also includes allowing the use of a general purpose processor, wherein radio-frequency (RF) processing, including beamforming is performed in software.

It should be noted that the various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams". Also, forming of images may be performed using channel combinations that may originate from more than one transmit event.

In various embodiments, ultrasound processing to form images is performed, for example, ultrasound beamforming, such as receive beamforming, is performed in software, hardware, or a combination thereof. One implementation of an ultrasound system having a software beamformer architecture formed in accordance with various embodiments is shown in FIG. 1, which illustrates a simplified block diagram of an ultrasound system 30. The ultrasound system 30 is configured to acquire ultrasound data using a probe 32, wherein transmission and reception functionality, such as transmission and reception of ultrasound signals are provided by a front end 34, which as illustrated does not include a hardware implemented receive beamformer. However, it should be noted that a hardware implemented receive beamformer optionally may be provided to perform, for example, a partial beamforming. The front end 34 generally includes a transmitter/receiver, which may be implemented in, for example, an application specific integrated circuit (ASIC) or a field-programmable gate array (FPGA).

The front end 34 is connected to a back end 36, for example, via one or more communication lines 38, which may include one or more buses, such as a Peripheral Component Interconnect Express (PCIe) bus or other bus (e.g., a high bandwidth bus having at least several GB/sec. transfer rate). The communication line(s) 38 communicates ultrasound data from the front end 34 to the back end 36, and may include one or more data channels. The back end 36 generally includes processing units, which include a software implemented beamformer and an IQ/RF processor as described in more detail below. These processing functions may be performed by a general purpose CPU or GPU.

In various embodiments, the amount of data transmitted from the front end 34 to the back end 36 is reduced such that a lower ultrasound data sample and/or transfer rate is used. For example, the ultrasound system 30 may include a 12-bit analog to digital converter (ADC) that is sampling data from 256 ultrasound channels, with a sample rate of 65 MHz, producing a data rate of about 25 GB/s. In order to transfer data at 25 GB/s, more than 50 lines of PCIe generation 2 (PCIe G2) would be needed, and that is not capable of being transferred over the buses. However, in accordance with various embodiments, methods for data rate reduction are provided, such that reduced data rate data can be transferred over the buses. Thus, various embodiments provide a data sample rate or transfer rate reduction that allows data to be communicated using lower bandwidth data channels.

The data flow from ultrasound front end channels, which may include using the ADC, to data processors, such as back end processors performing beamforming calculation, tissue processing, etc., is thereby controlled. In some embodiments, the data communicated from the front end 34 to the back end 36 includes controlling the data communicated to transfer only that data which is needed for the particular processing operation and/or based on a communication bandwidth. The ultrasound system 30 may be used to perform different kinds of ultrasound scans for different applications to acquire ultrasound image data. For example, in some embodiments, the ultrasound system 30 operates to perform real-time four-dimensional (4D) scanning that acquires multiple beams simultaneously or concurrently. The ultrasound system 30 in various embodiments includes the software implemented beamformer implemented in a general purpose processor (e.g., CPU or GPU) that receives data from all of the communication lines 38. Thus, data transfer from all of the communication lines 38 are provided in some embodiments, with the general purpose processor performing beamforming processing, such as beamforming calculations using any suitable beamforming method.

It should be noted that software beamforming includes performing any type of beamforming technique, which may include performing beamforming techniques in software that can be performed in hardware. It also should be noted that when reference is made herein to beamforming techniques, this generally refers to any type of image forming that may be performed by the ultrasound system. Accordingly, the various embodiments may be implemented in connection with forming images whether or not beams are formed.

Various embodiments use apriori information or knowledge regarding signal bandwidth (e.g., input signal carrier frequency and bandwidth) in the ultrasound data path to control the transfer of that ultrasound data. Additionally, apriori information or knowledge regarding the distribution of relevant or needed data among the system channels in the time domain is used to control the transfer of ultrasound data.

Figure 2:
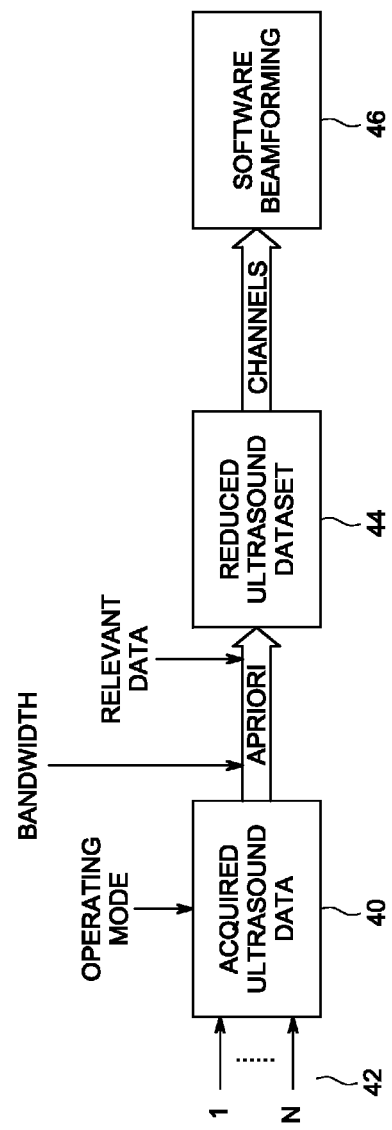
FIG. 2 is a block diagram illustrating a data communication process performed in accordance with various embodiments.
Figure 3:
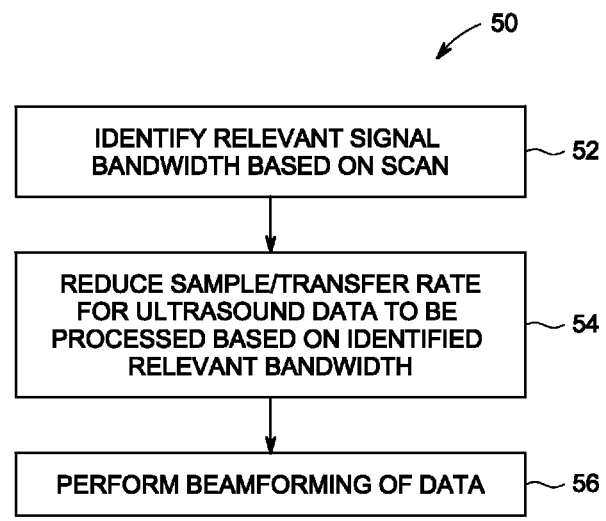
FIG. 3 is a flowchart of a method for digital demodulation in accordance with various embodiments.

For example, as illustrated in FIG. 2, showing an ultrasound processing work flow performed in accordance with various embodiments for controlling the communication of ultrasound data, based on an operating mode of the ultrasound system or probe, ultrasound data 40 is acquired. The acquired ultrasound data 40 is received via a plurality of receive channels 42. A reduced ultrasound data set 44 is identified for communicating between the front end of the ultrasound system to the processing units. The reduced ultrasound data set 44 is a set of ultrasound data based on the acquired ultrasound data 40 and having a reduced amount of data to be communicated for processing. The determination of the data to include in the reduced ultrasound data set 44 may be based on one or more factors, for example, bandwidth usage or requirements, the relevant data (e.g., clinically relevant data) needed for processing, etc. The reduced ultrasound data set 44 is then communicated to the processing units, for example, to process the data, such as to perform software beamforming 46. It should be noted that the communicated reduced ultrasound data set 44 includes data for all data channels corresponding to each of the receive channels.

Methods for controlling the communication of the ultrasound data may use digital demodulation and filtering and/or variable decimation, among other methods, for transfer of data for subsequent beamforming. Various methods for controlling the communication in ultrasound data are described in more detail below.

In one embodiment, a method 50 is provided for data rate reduction that includes digital demodulation, filtering and decimation. The method 50 is performed for every channel of ultrasound data for subsequent beamforming. In particular, the method 50 includes identifying the relevant signal bandwidth for a particular scan at 52 and then at 54 reducing the sample rate for the ultrasound data (to be processed) based on the identified relevant bandwidth.

For example, in adult cardiac harmonic imaging, the relevant signal bandwidth is less than 2 MHz (while the ADC is sampling at, for example, 50 MHz). Accordingly, the relevant bandwidth may be defined based on the relevant bandwidth frequency, which may include a predetermined variance or margin above that bandwidth frequency, which in this example, may be an additional 1 MHz. Accordingly, the sample rate of the complex IQ signal from the ultrasound system receiver may be set at 3 MHz. However, it should be noted that other minimal frequency bandwidth levels may be defined by changing the variance or margin as desired or needed.

In various embodiments, digital demodulation of the signals is accomplished by multiplying the signal by a cosine factor to create an in-phase (I) component and by a sine factor to create a quadrature (Q) component for the IQ signal. The factors may be based on the demodulation frequency for the relevant signal bandwidth. For example, the signal may be multiplied by $\cos(\omega_d t)$ and $\sin(\omega_d t)$, where $\omega_d = 2\pi F_d$, and $F_d$ is the demodulation frequency. It should be noted that the demodulation frequency in some embodiments is constant along the signal vector and is the same for all data channels. However, the demodulation frequency in other embodiments may vary.

Thereafter, the signal is filtered (as part of the demodulation), with decimation of the data performed. For example, a demodulation filter may be provided to limit the bandwidth of the baseband demodulated signal prior to decimation. The demodulation filter in various embodiments is programmable and operates as a low pass filter, for example, is implemented as a low pass finite impulse response (FIR) filter with a predetermined number of taps (e.g., sixteen taps) per decimation. It should be noted that the decimation factor can vary depending on the scanning mode and signal bandwidth. The decimation factor also can vary based on whether imaging is performed in a fundamental or second harmonic mode. For example, the demodulation filter may be implemented such that only the second harmonic component of the acquired signal is transferred for subsequent beamforming. Additionally, the decimation factor and the demodulation frequency can vary from vector to vector, but are the same for all channels and constant during a vector. It should be noted that the filtering in various embodiments sets the bandwidth of the demodulator.

Beamforming, and in particular, beamforming in software is then performed on the data at 56. Thus, the part of the signal spectrum that is not relevant or needed for the beamforming or particular imaging is removed prior to beamforming. For example, the center frequency for a 2 MHz sampling frequency is about 3.5 MHz. The various embodiments move the center frequency to zero and the filter is programmed to pass the relevant frequency band of interest, namely, the relevant frequency bandwidth.

It should be noted that in various embodiments, demodulation includes multiplication by a complex exponential and low-pass filtering, such as to extract a complex signal envelope.

Figure 4:
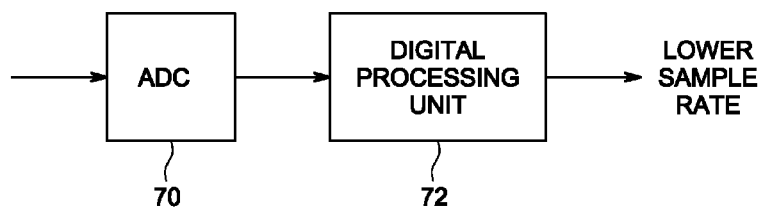
FIG. 4 is an exemplary blocking diagram illustrating a data communication process performed in accordance with the method illustrated in FIG. 3.

Thus, the decimation ratio may be varied or controlled based on the bandwidth of the signal that is expected, with the decimation and filtering configured accordingly. As illustrated in FIG. 4, data from a plurality of receive channels is received at an ADC 70 and digitally demodulated, which may include filtering and decimation, before transmission to one or more digital processing units 72 for processing, such as beamforming in software. The digital processing is performed in the channel domain and the resulting signal has a lower sample rate.

In the method 50, the bit-width may be based on the decimation ratio. Thus, a variable bit-width may be provided. Accordingly, different bit-widths or bit-digits may be selected for the data set. It should be noted that the more decimating that is performed, the higher the dynamic range of the signal. To preserve a particular dynamic range, more bits per sample may be communicated.

The method 50 reduces the transfer data rate by digital demodulation of the data in every receive channel, with subsequent filtering and decimation. The filtering and the decimation are variable and depend on the relevant signal bandwidth. The method 50 provides the reduction of the data rate by reducing the sample rate, such that only the relevant signal bandwidth is transferred for subsequent processing (e.g., beamforming).

The method 50 also may be applied to Pulse-Wave (PW) Doppler imaging with even lower bandwidth and data reduction factors. Additionally, it should be noted that the transfer sampling rate does not limit the maximum frequency of the received signals and only affects the signal bandwidth in various embodiments.

Figure 5:
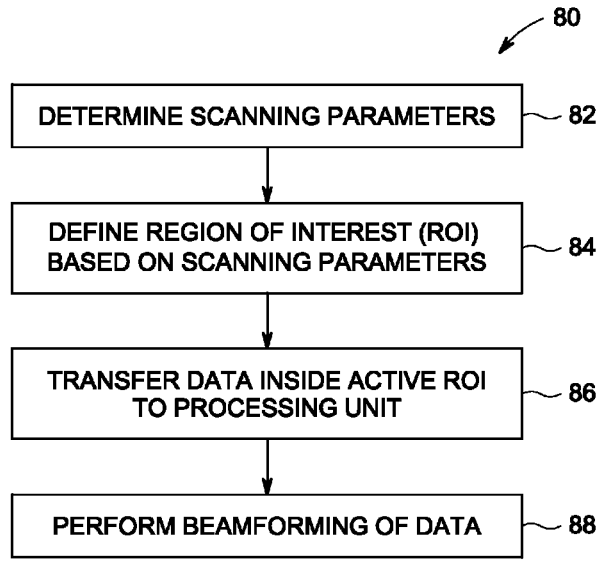
FIG. 5 is a flowchart of another method for digital demodulation in accordance with various embodiments.

In another method 80, as illustrated in FIG. 5, a region of interest (ROI) in the channel time space is defined to reduce the transfer data rate of data to be beamformed. In the method 80, the scanning parameters for a scan are determined at 82. For example, the scanning parameters may include focal zones, expanding aperture, imaging mode, etc. The scanning parameters are used to define an ROI at 84. The ROI is used to limit the data for the channels that is communicated for processing. For example, based on the scanning parameters, an ROI is chosen that defines the channels and time slots for which data should be communicated to be processed, with the other channels or time slots of data not communicated for processing (e.g., discarded).

Data is then transferred from inside an active ROI at 86. Accordingly, in the channel domain, only data from certain channels within certain time slots are transferred. For example, if the ROI defines a receive aperture, only data received within the aperture is communicated and data outside the aperture not communicated. Thereafter, beamforming, for example, beamforming in software is performed at 88.

Thus, data relevant for beamforming is transferred based on the defined ROI as determined by one or more scanning parameters. For example, in an expanding aperture application, the aperture expands along time along vectors (e.g., vector beams), thereby changing the amount of data that is communicated for processing. As another example, more channels of data are communicated for processing as scanning is performed at deeper depths of the object being scanned.

The method 80, thus, reduces the transfer data rate by definition of an ROI in the channels-time space, and by transferring the data only from inside the ROI. The ROI defines, for every channel, the starting time relative to the beginning of the vector, and the duration of the data transfer. The ROI definition depends on one or more scanning parameters, such as focal zones, expanding aperture, imaging mode (B, color flow, PW Doppler), etc. The ROI in various embodiments is calculated by software, and then the front-end hardware is set up or programmed to transfer the data only from inside the active ROI. Reduced data transfer results, such as for scanning with linear and curved arrays, for example, for scanning with a linear array probe, with three focal zones, wherein the resulting beam is combined from three focal zones. The data transferred is limited to signals received from the three focal zones as opposed to transferring all the data and only processing data related to the three focal zones.

Figure 6:
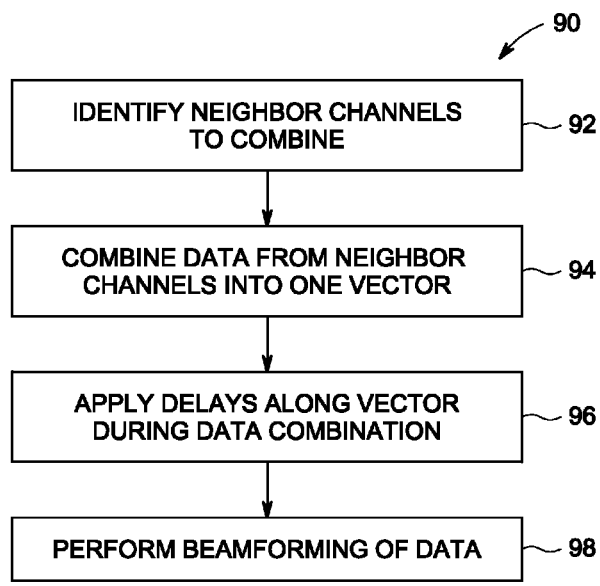
FIG. 6 is a flowchart of another method for digital demodulation in accordance with various embodiments.

In another method 90, as illustrated in FIG. 6, a plurality of channels to combine is identified at 92. The identification includes determining a plurality of neighbor or adjacent channels, for example, channels corresponding to adjacent receive elements of the ultrasound probe. The determination may be based on a grouping of receive elements and/or a predetermined number of channels to combine. Data from the neighbor channels is then combined into a single vector at 94. The combination of the data from the multiple channels into a single vector may be performed using any suitable vector combination method. While combining the data, delays along the vector are applied at 96. For example, relevant delays (e.g., phase rotation) are applied and change along the vector. Thereafter, the data is communicated for beamforming, for example, beamforming in software is performed at 98.

The method 90, thus, reduces the transfer data rate by combining data from multiple channels (e.g., four channels), which reduces the number of channels of data that is transferred. The method 90 performs a digital sub-aperture beamforming wherein phase rotation may be used to combine the data based on the relevant delays.

Figure 7:
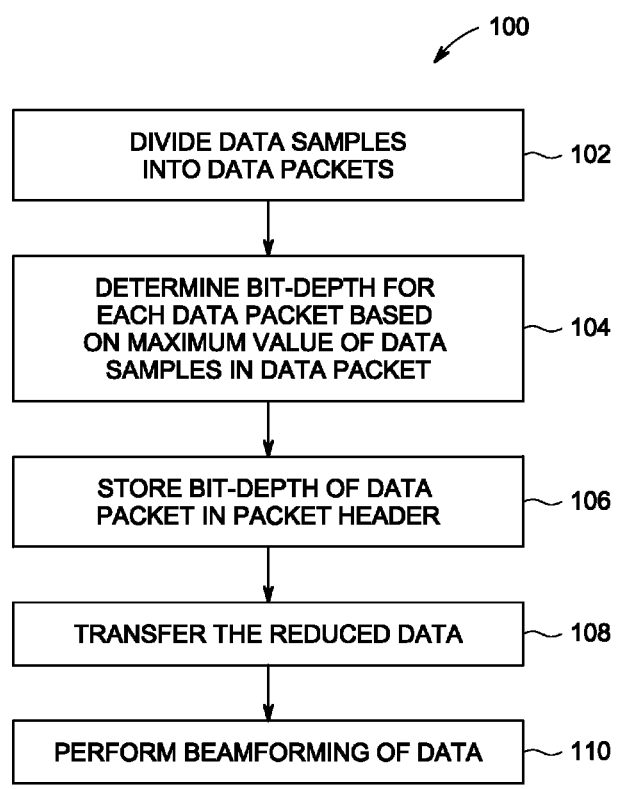
FIG. 7 is a flowchart of another method for digital demodulation in accordance with various embodiments.

In another method 100, as illustrated in FIG. 7, the data, and in particular, the data samples to be communicated for processing, are divided into a plurality of data packets at 102. The size of each of the data packets, namely the number of data samples to include in each data packet may be predetermined and/or variable. For example, seven bits may be used if the maximum value is 100.

Thereafter, the bit depth for each of the data packets is determined at 104, which is based on the maximum value for the data samples in each of the data packets. Thus, each data packet has a different bit-depth value based on the maximum depth of the data samples in that packet. The determined bit-depth for each data packet is then stored at 106, for example, stored in the packet header for each data packet. The reduced data is then transferred at 108, for example, from a front end to a back end of the ultrasound system for beamforming. Thereafter, beamforming is performed at 110, for example, software beamforming is performed.

The method 100, thus, reduces the transfer data rate by reducing the number of bits for the data packets transferred, which reduces the amount of data that is transferred. Accordingly, data compression of demodulated IQ data using packet based variable bit-depths is provided. The method 100 performs encoding and decoding and uses the information that the ultrasound signal SNR reduces along the vector, such that signals acquired from a deeper distance in an object require fewer bits of data. As discussed above, seven bits may be used if the maximum value is 100 instead of twelve bits, such as are received from a 12 bit ADC.

It should be noted that the various methods described herein may be performed separately or may be combined to increase the data rate reduction factor. For example, in some embodiments, one of the methods described herein is used to reduce the transferred data rate for beamforming. In other embodiments, two or more methods may be performed in any order to further reduce the transferred data rate for beamforming.

In various embodiments, the receive beamformer uses down-converted IQ data and not the original RF data sampled by the ADC. However, in other embodiments the original RF data or combinations of different data may be used. The down-conversion (demodulation) of the RF data is performed on each of the receive channels and may be performed, for example, in an ASIC performing the ADC conversions. As described in more detail herein, after demodulation the signal can be filtered and then decimated based on the signal bandwidth.

Figure 8:
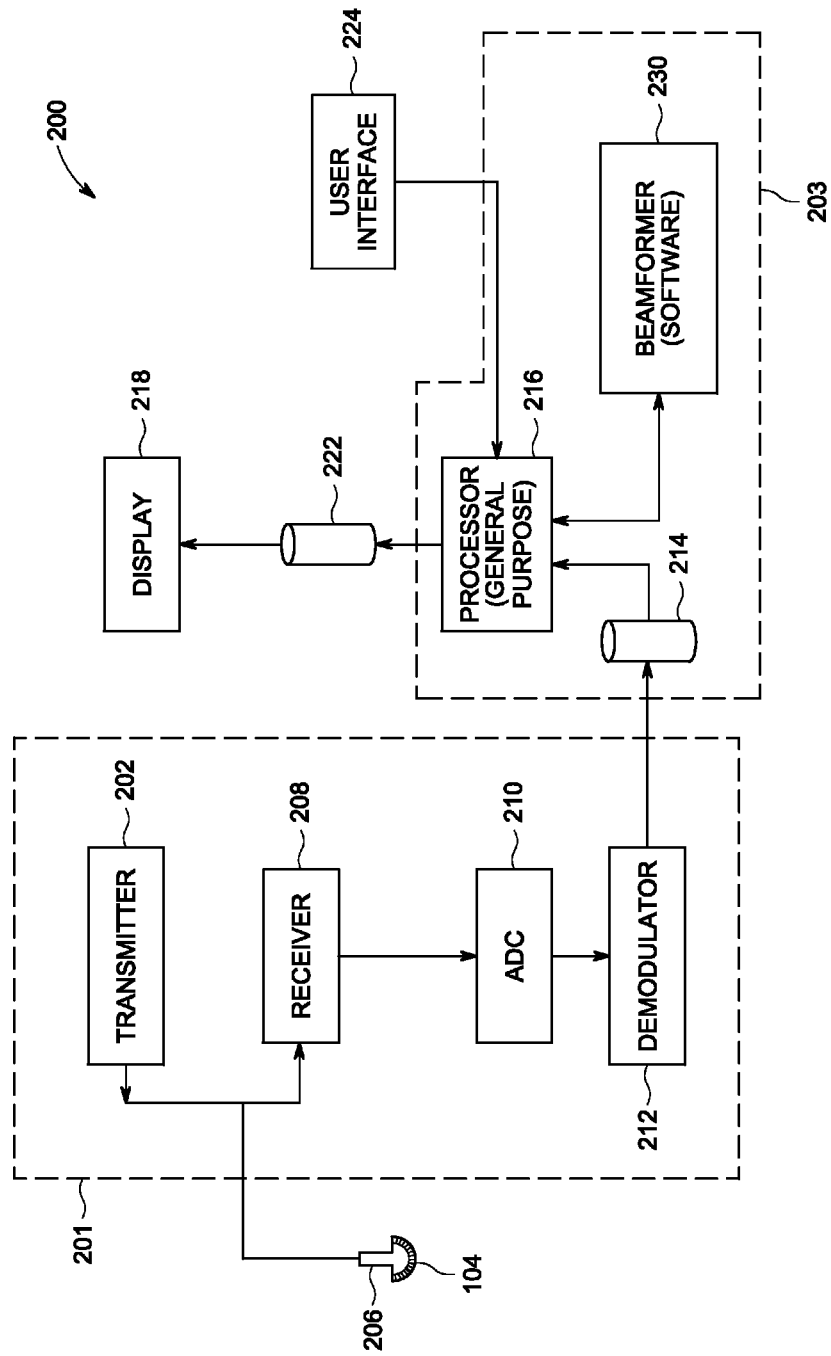
FIG. 8 is a block diagram of an ultrasound system in connection with which various embodiments may be implemented.

The various embodiments of demodulation for ultrasound imaging, particularly wherein software beamforming is provided, may be implemented in an ultrasound system 200 as illustrated in FIG. 8. It should be noted that the various embodiments for reducing data transfer rates, for example, using the various demodulation techniques may be implemented in different portions or components of the ultrasound system 200. For example, digital demodulation may be performed in an ASIC that also implements the ADC or may be performed in other hardware or software, and which may be performed in the front end or back end of the system.

In particular, FIG. 8 is a block diagram showing an ultrasound system 200 that operates to perform digital demodulation of ultrasound data for beamforming, illustrated as software beamforming, in accordance with various embodiments. The software beamforming may be implemented, for example, by a processor executing instructions on a tangible, non-transitory computer readable medium. The ultrasound system 200 is configured to acquire ultrasound data using a probe 206, wherein transmission and reception of ultrasound signals are provided by a front end 201, which as illustrated does not include a hardware implemented receive beamformer. However, it should be noted that a hardware implemented receive beamformer optionally may be provided to perform some beamforming. The front end 201 is connected to a back end 203 via a plurality of data channels that communicate ultrasound data from the front end 201 to the back end 203.

The ultrasound system 200 is capable of electrical or mechanical steering of a soundbeam (such as in 3D space) and is configurable to acquire information corresponding to a plurality of 2D representations or images (or optionally 3D and 4D images) of a region of interest (ROI) in a subject or patient, which may be defined or adjusted as described in more detail herein. The ultrasound system 200 is configurable to acquire 2D images, for example, in one or more planes of orientation.

The ultrasound system 200 includes a transmitter 202 that, under the guidance of a beamformer (transmit beamformer), drives an array of elements 204 (e.g., piezoelectric elements) within a probe 206 to emit pulsed ultrasonic signals into a body. A variety of geometries may be used. The ultrasonic signals are back-scattered from structures in the body, like blood cells or muscular tissue, to produce echoes that return to the elements 204. The echoes are received by a receiver 208 and then communicated to an ADC 210 and demodulator 212, which may be different components or implemented in a single component, for example, in an ASIC. The demodulator 212 performs digital demodulation, and optionally filtering and decimation as described in more detail herein. The demodulated (or down-sampled) ultrasound data may be stored in a memory 214.

The demodulator 212, demodulates the RF signal to form IQ data pairs representative of the echo signals, which in various embodiments have a reduced data transfer rate that the transfer rate of the ADC 210. The RF or IQ signal data may then be routed directly to the memory 214 for storage. In some embodiments, a hardware receive beamformer optionally may be provided in the front end 201. In an alternative embodiment, the probe 206 optionally includes a 2D array with sub-aperture receive beamforming inside the probe.

The demodulator 112 may generate different data types, e.g. B-mode, color Doppler (velocity/power/variance), tissue Doppler (velocity), and Doppler energy, for multiple scan planes or different scanning patterns. For example, the demodulator 112 may generate tissue Doppler data for multi-scan planes. The demodulator 112 gathers the information (e.g. I/Q, B-mode, color Doppler, tissue Doppler, and Doppler energy information) related to multiple data slices and stores the data information, which may include time stamp and orientation/rotation information, in the memory 214.

The ultrasound system 200 also includes a processor 216 to process the acquired ultrasound information (e.g., RF signal data or IQ data pairs) and prepare frames of ultrasound information for display on display 218, with the image quality or resolution improved as described in more detail herein. The processor 216 is adapted to perform one or more processing operations according to a plurality of selectable ultrasound modalities on the acquired ultrasound data. The processor 216 also performs beamforming operations using a beamformer 230, which in the illustrated embodiment is software.

The processor 216 is connected to a user interface 224 (which may include a mouser, keyboard, etc.) that may control operation of the processor 216 as explained below in more detail. A display 218 includes one or more monitors that present patient information, including diagnostic ultrasound images to the user for diagnosis and analysis. One or both of memory 214 and memory 222 may store two-dimensional (2D) or three-dimensional (3D) data sets of the ultrasound data, where such 2D and 3D data sets are accessed to present 2D (and/or 3D or 4D images), which may be in different states of beamforming. The images may be modified and the display settings of the display 218 also manually adjusted using the user interface 224.

The beamformer 230 shown connected to the processor 216 may be software running on the processor 216 or hardware provided as part of the processor 216. The beamformer 230, performs receive beamforming as described in more detail herein and outputs an RF signal. The beamformer 230 may delay, apodize and sum each electrical signal with other received signals. The summed signals represent echoes from the ultrasound beams or lines.

It should be noted that although the various embodiments may be described in connection with an ultrasound system, the methods and systems are not limited to ultrasound imaging or a particular configuration thereof. The various embodiments may be implemented in connection with different types of imaging systems, including, for example, multi-modality imaging systems having an ultrasound imaging system and one of an x-ray imaging system, magnetic resonance imaging (MRI) system, computed-tomography (CT) imaging system, positron emission tomography (PET) imaging system, among others. Further, the various embodiments may be implemented in non-medical imaging systems, for example, non-destructive testing systems such as ultrasound weld testing systems or airport baggage scanning systems.

Figure 9:
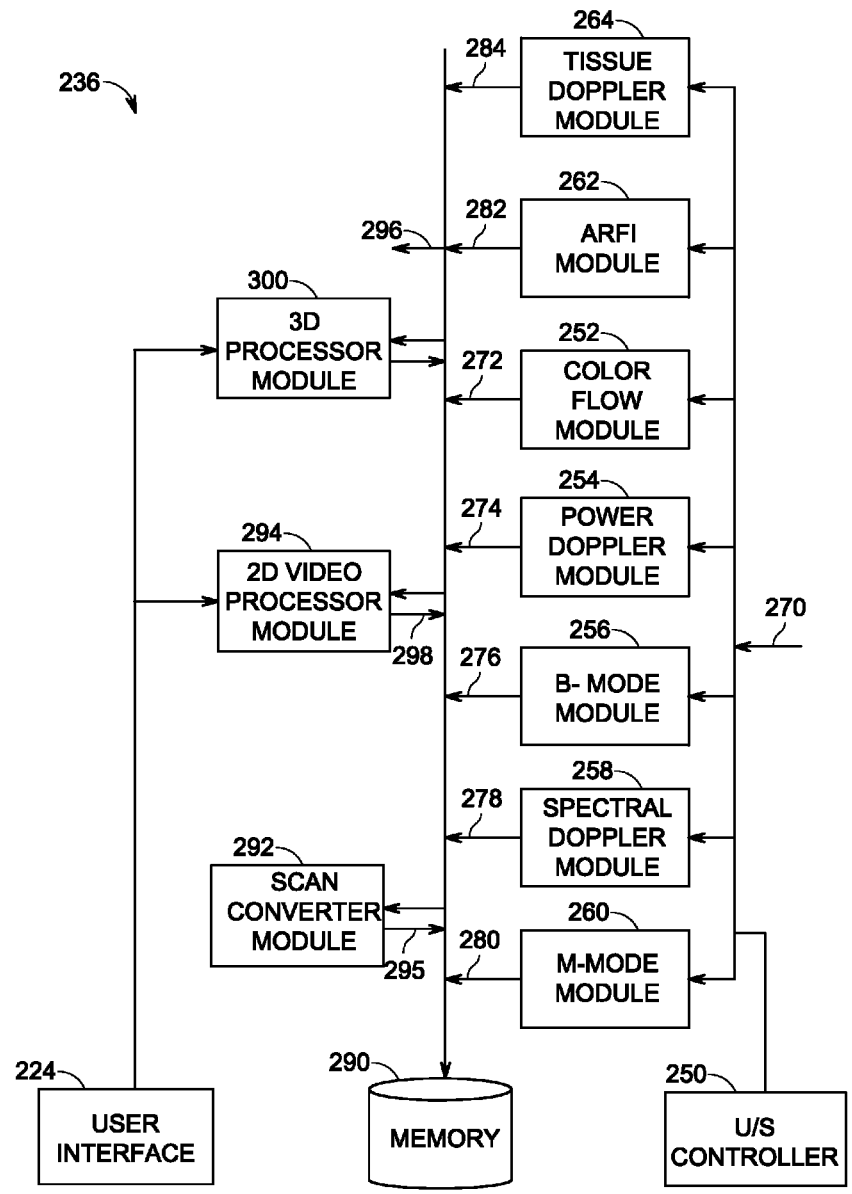
FIG. 9 is a block diagram of an ultrasound processor module of the ultrasound system of FIG. 8 formed in accordance with various embodiments.

FIG. 9 illustrates an exemplary block diagram of an ultrasound processor module 236, which may be embodied as the processor 216 of FIG. 8 or a portion thereof. The ultrasound processor module 236 is illustrated conceptually as a collection of sub-modules, but may be implemented utilizing any combination of dedicated hardware boards, DSPs, processors, etc. Alternatively, the sub-modules of FIG. 9 may be implemented utilizing an off-the-shelf PC with a single processor or multiple processors, with the functional operations distributed between the processors. As a further option, the sub-modules of FIG. 9 may be implemented utilizing a hybrid configuration in which certain modular functions are performed utilizing dedicated hardware, while the remaining modular functions are performed utilizing an off-the shelf PC and the like. The sub-modules also may be implemented as software modules within a processing unit.

The operations of the sub-modules illustrated in FIG. 9 may be controlled by a local ultrasound controller 250 or by the processor module 236. The sub-modules 252-264 perform mid-processor operations. The ultrasound processor module 236 may receive ultrasound data 270 in one of several forms. In the embodiment of FIG. 9, the received ultrasound data 270 constitutes I,Q data pairs representing the real and imaginary components associated with each data sample. The I,Q data pairs are provided to one or more of a color-flow sub-module 252, a power Doppler sub-module 254, a B-mode sub-module 256, a spectral Doppler sub-module 258 and an M-mode sub-module 260. Optionally, other sub-modules may be included such as an Acoustic Radiation Force Impulse (ARFI) sub-module 262 and a Tissue Doppler (TDE) sub-module 264, among others.

Each of sub-modules 252-264 are configured to process the I,Q data pairs in a corresponding manner to generate color-flow data 272, power Doppler data 274, B-mode data 276, spectral Doppler data 278, M-mode data 280, ARFI data 282, and tissue Doppler data 284, all of which may be stored in a memory 290 (or memory 214 or memory 222 shown in FIG. 8) temporarily before subsequent processing. For example, the B-mode sub-module 256 may generate B-mode data 276 including a plurality of B-mode image planes, such as in a biplane or triplane image acquisition as described in more detail herein.

The data 272-284 may be stored, for example, as sets of vector data values, where each set defines an individual ultrasound image frame. The vector data values are generally organized based on the polar coordinate system.

A scan converter sub-module 292 accesses and obtains from the memory 290 the vector data values associated with an image frame and converts the set of vector data values to Cartesian coordinates to generate an ultrasound image frame 295 formatted for display. The ultrasound image frames 295 generated by the scan converter module 292 may be provided back to the memory 290 for subsequent processing or may be provided to the memory 214 or the memory 222.

Once the scan converter sub-module 292 generates the ultrasound image frames 295 associated with, for example, B-mode image data, and the like, the image frames may be restored in the memory 290 or communicated over a bus 296 to a database (not shown), the memory 214, the memory 222 and/or to other processors.

The scan converted data may be converted into an X,Y format for video display to produce ultrasound image frames. The scan converted ultrasound image frames are provided to a display controller (not shown) that may include a video processor that maps the video to a grey-scale mapping for video display. The grey-scale map may represent a transfer function of the raw image data to displayed grey levels. Once the video data is mapped to the grey-scale values, the display controller controls the display 218 (shown in FIG. 8), which may include one or more monitors or windows of the display, to display the image frame. The image displayed in the display 118 is produced from image frames of data in which each datum indicates the intensity or brightness of a respective pixel in the display.

Referring again to FIG. 9, a 2D video processor sub-module 294 combines one or more of the frames generated from the different types of ultrasound information. For example, the 2D video processor sub-module 294 may combine a different image frames by mapping one type of data to a grey map and mapping the other type of data to a color map for video display. In the final displayed image, color pixel data may be superimposed on the grey scale pixel data to form a single multi-mode image frame 298 (e.g., functional image) that is again re-stored in the memory 290 or communicated over the bus 296. Successive frames of images may be stored as a cine loop in the memory 290 or memory 222 (shown in FIG. 8). The cine loop represents a first in, first out circular image buffer to capture image data that is displayed to the user. The user may freeze the cine loop by entering a freeze command at the user interface 224. The user interface 224 may include, for example, a keyboard and mouse and all other input controls associated with inputting information into the ultrasound system 200 (shown in FIG. 8).

A 3D processor sub-module 300 is also controlled by the user interface 124 and accesses the memory 290 to obtain 3D ultrasound image data and to generate three dimensional images, such as through volume rendering or surface rendering algorithms as are known. The three dimensional images may be generated utilizing various imaging techniques, such as ray-casting, maximum intensity pixel projection and the like.

Figure 10:
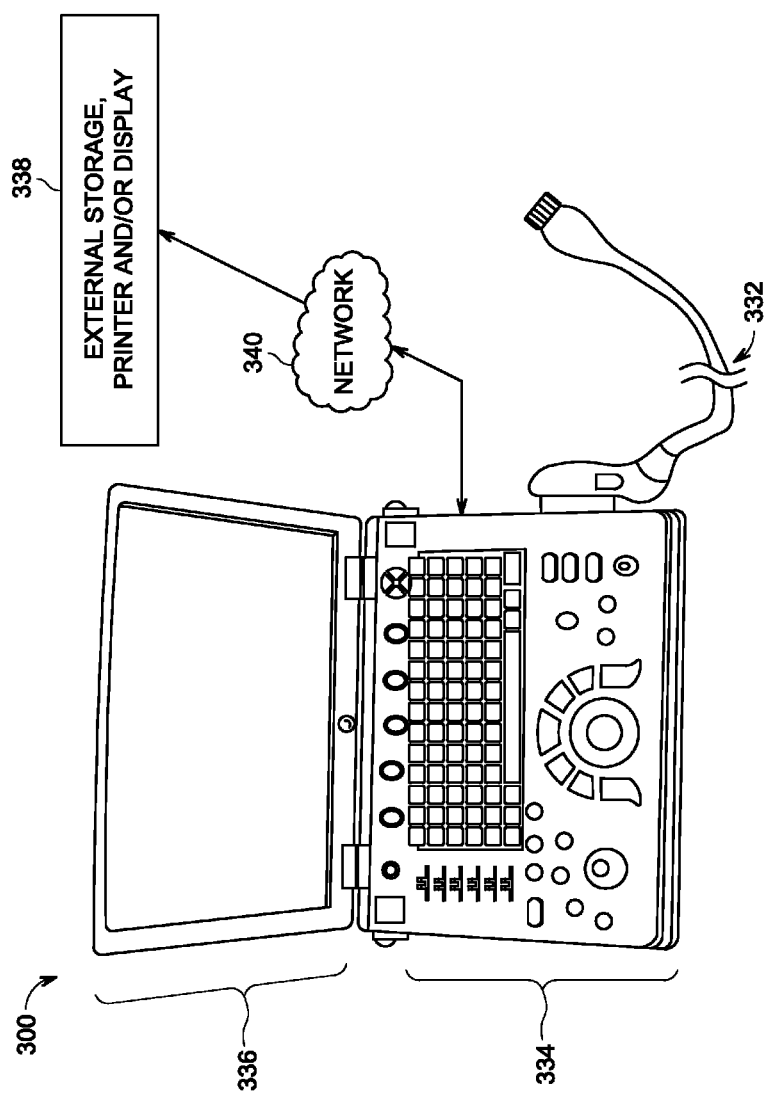
FIG. 10 is a diagram illustrating a three-dimensional (3D) capable miniaturized ultrasound system in which various embodiments may be implemented.
Figure 11:
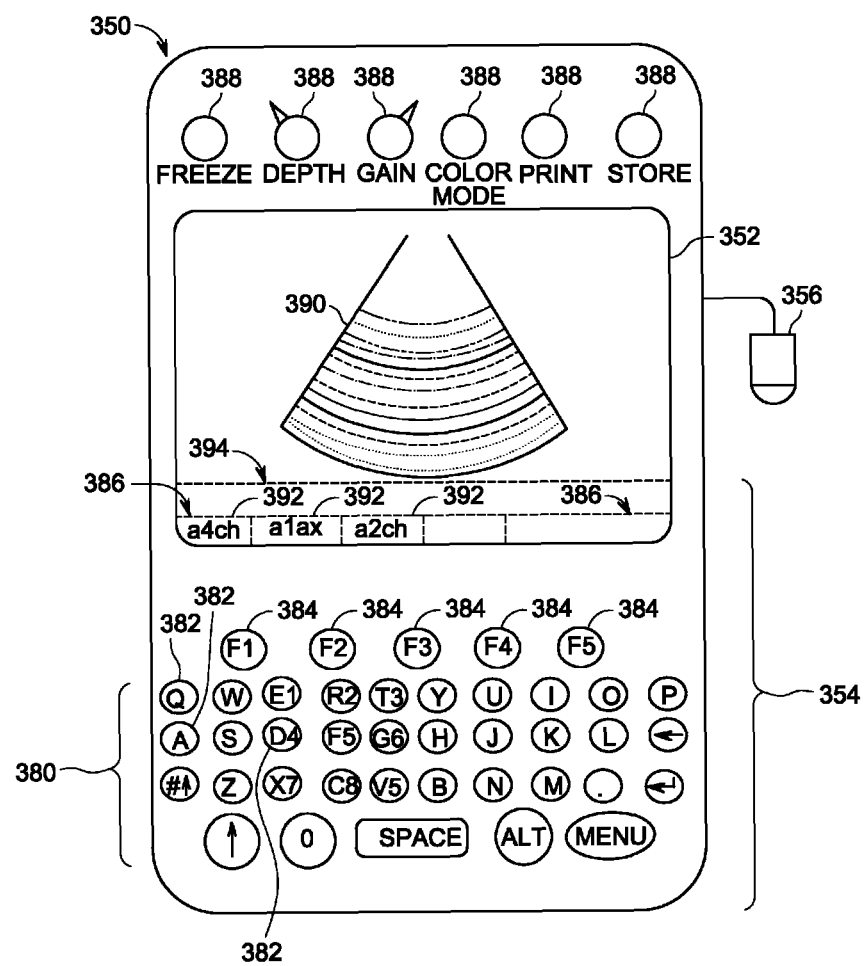
FIG. 11 is a diagram illustrating a 3D capable hand carried or pocket-sized ultrasound imaging system in which various embodiments may be implemented.
Figure 12:
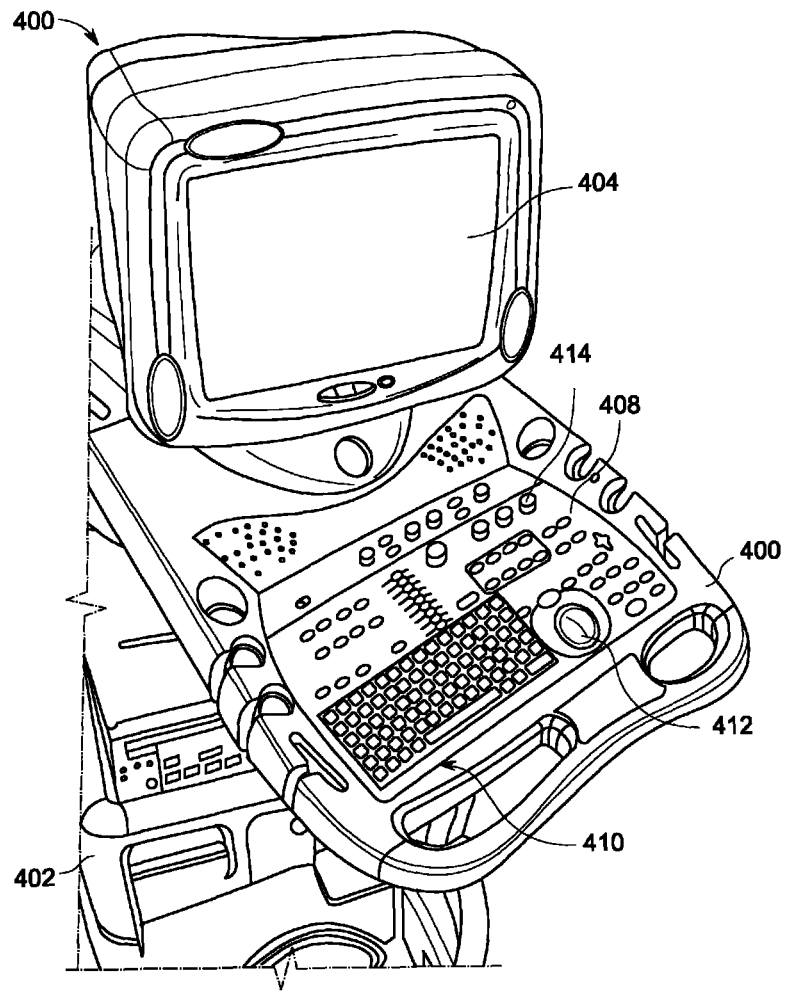
FIG. 12 is a diagram illustrating a 3D capable console type ultrasound imaging system in which various embodiments may be implemented.

The ultrasound system 200 of FIG. 8 may be embodied in a small-sized system, such as laptop computer or pocket sized system as well as in a larger console-type system. FIGS. 10 and 11 illustrate small-sized systems, while FIG. 12 illustrates a larger system.

FIG. 10 illustrates a 3D-capable miniaturized ultrasound system 330 having a probe 332 that may be configured to acquire 3D ultrasonic data or multi-plane ultrasonic data. For example, the probe 332 may have a 2D array of elements 204 as discussed previously with respect to the probe 206 of FIG. 8. A user interface 334 (that may also include an integrated display 336) is provided to receive commands from an operator. As used herein, "miniaturized" means that the ultrasound system 330 is a handheld or hand-carried device or is configured to be carried in a person's hand, pocket, briefcase-sized case, or backpack. For example, the ultrasound system 330 may be a hand-carried device having a size of a typical laptop computer. The ultrasound system 330 is easily portable by the operator. The integrated display 336 (e.g., an internal display) is configured to display, for example, one or more medical images.

The ultrasonic data may be sent to an external device 338 via a wired or wireless network 340 (or direct connection, for example, via a serial or parallel cable or USB port). In some embodiments, the external device 338 may be a computer or a workstation having a display, or the DVR of the various embodiments. Alternatively, the external device 338 may be a separate external display or a printer capable of receiving image data from the hand carried ultrasound system 330 and of displaying or printing images that may have greater resolution than the integrated display 336.

FIG. 11 illustrates a hand carried or pocket-sized ultrasound imaging system 350 wherein the display 352 and user interface 354 form a single unit. By way of example, the pocket-sized ultrasound imaging system 350 may be a pocket-sized or hand-sized ultrasound system approximately 2 inches wide, approximately 4 inches in length, and approximately 0.5 inches in depth and weighs less than 3 ounces. The pocket-sized ultrasound imaging system 350 generally includes the display 352, user interface 354, which may or may not include a keyboard-type interface and an input/output (I/O) port for connection to a scanning device, for example, an ultrasound probe 356. The display 352 may be, for example, a 320×320 pixel color LCD display (on which a medical image 390 may be displayed). A typewriter-like keyboard 380 of buttons 382 may optionally be included in the user interface 354.

Multi-function controls 384 may each be assigned functions in accordance with the mode of system operation (e.g., displaying different views). Therefore, each of the multi-function controls 384 may be configured to provide a plurality of different actions. Label display areas 386 associated with the multi-function controls 384 may be included as necessary on the display 352. The system 350 may also have additional keys and/or controls 388 for special purpose functions, which may include, but are not limited to "freeze," "depth control," "gain control," "color-mode," "print," and "store."

One or more of the label display areas 386 may include labels 392 to indicate the view being displayed or allow a user to select a different view of the imaged object to display. The selection of different views also may be provided through the associated multi-function control 384. The display 352 may also have a textual display area 394 for displaying information relating to the displayed image view (e.g., a label associated with the displayed image).

It should be noted that the various embodiments may be implemented in connection with miniaturized or small-sized ultrasound systems having different dimensions, weights, and power consumption. For example, the pocket-sized ultrasound imaging system 350 and the miniaturized ultrasound system 330 may provide the same scanning and processing functionality as the system 200 (shown in FIG. 8).

FIG. 12 illustrates an ultrasound imaging system 400 provided on a movable base 402. The portable ultrasound imaging system 400 may also be referred to as a cart-based system. A display 404 and user interface 406 are provided and it should be understood that the display 404 may be separate or separable from the user interface 406. The user interface 406 may optionally be a touchscreen, allowing the operator to select options by touching displayed graphics, icons, and the like.

The user interface 406 also includes control buttons 408 that may be used to control the portable ultrasound imaging system 400 as desired or needed, and/or as typically provided. The user interface 406 provides multiple interface options that the user may physically manipulate to interact with ultrasound data and other data that may be displayed, as well as to input information and set and change scanning parameters and viewing angles, etc. For example, a keyboard 410, trackball 412 and/or multi-function controls 414 may be provided.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, the embodiments are by no means limiting and are exemplary embodiments. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A method for demodulating ultrasound data, the method comprising:
receiving ultrasound data from a plurality of channels of an ultrasound probe in an ultrasound system;
reducing a sample rate of the received ultrasound data for the plurality of channels using digital demodulation, wherein a demodulation frequency for at least one of the plurality of channels is different than a demodulation frequency for at least one other of the plurality of channels;
communicating the reduced sample rate ultrasound data to a processor of the ultrasound system; and
performing processing of the reduced sample rate ultrasound data using the processor, wherein the processing includes beamforming.

2. A method in accordance with claim 1 further comprising one of filtering and decimating to reduce the data sample rate of the ultrasound data before beamforming.

3. A method in accordance with claim 1 further comprising using one of bandwidth information and relevant data information to reduce the sample rate.

4. A method for processing ultrasound data, the method comprising:
receiving ultrasound data from a plurality of channels of an ultrasound probe in an ultrasound system;
identifying a relevant signal bandwidth for the received ultrasound data and using the identified relevant signal bandwidth to demodulate the received ultrasound data;
digitally demodulating the received ultrasound data such that a data transfer rate of the digitally demodulated ultrasound data is lower than a data transfer rate of the received ultrasound data before digital demodulation, the data transfer rate of the digitally demodulated ultrasound data determined using signal bandwidth information and relevant data information; and
processing the digitally demodulated ultrasound data to form an ultrasound image, wherein the processing is performed using a processor of the ultrasound system.

5. A method for processing ultrasound data, the method comprising:
receiving ultrasound data from a plurality of channels of an ultrasound probe in an ultrasound system;
identifying relevant ultrasound data and using the relevant ultrasound data to demodulate the received ultrasound data;
digitally demodulating the received ultrasound data such that a data transfer rate of the digitally demodulated ultrasound data is lower than a data transfer rate of the received ultrasound data before digital demodulation, the data transfer rate of the digitally demodulated ultrasound data determined using signal bandwidth information and relevant data information; and
processing the digitally demodulated ultrasound data to form an ultrasound image, wherein the processing is performed using a processor of the ultrasound system.

6. A method in accordance with claim 5 further comprising determining scanning parameters for the ultrasound scan and wherein the relevant ultrasound data is defined by a region of interest (ROI) based on the determined scanning parameters.

7. A method in accordance with claim 6 further comprising communicating only ultrasound data within the ROI for processing.

8. A method for processing ultrasound data, the method comprising:
receiving ultrasound data from a plurality of channels of an ultrasound probe in an ultrasound system;
digitally demodulating the received ultrasound data such that a data transfer rate of the digitally demodulated ultrasound data is lower than a data transfer rate of the received ultrasound data before digital demodulation, the data transfer rate of the digitally demodulated ultrasound data determined using signal bandwidth information and relevant data information, wherein the digital demodulating comprises dividing the received ultrasound data into a plurality of data packets;
varying a bit-depth for each of the plurality of data packets based on a maximum depth value; and
processing the digitally demodulated ultrasound data to form an ultrasound image, wherein the processing is performed using a processor of the ultrasound system.

* * * * *